(12) United States Patent
Huang et al.

(10) Patent No.: US 9,149,024 B2
(45) Date of Patent: Oct. 6, 2015

(54) ISLET1 (ISL1) AND HEARING LOSS

(75) Inventors: Mingqian Huang, Winchester, MA (US); Albena Kantardzhieva, Cambridge, MA (US); Zheng-Yi Chen, Somerville, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 13 days.

(21) Appl. No.: 13/380,143

(22) PCT Filed: Jun. 22, 2010

(86) PCT No.: PCT/US2010/039428
§ 371 (c)(1),
(2), (4) Date: May 15, 2012

(87) PCT Pub. No.: WO2011/005496
PCT Pub. Date: Jan. 13, 2011

(65) Prior Publication Data
US 2012/0222141 A1    Aug. 30, 2012

Related U.S. Application Data

(60) Provisional application No. 61/219,248, filed on Jun. 22, 2009.

(51) Int. Cl.
| | | |
|---|---|---|
| *A61K 38/00* | (2006.01) | |
| *C12Q 1/68* | (2006.01) | |
| *G01N 33/567* | (2006.01) | |
| *A01K 67/027* | (2006.01) | |
| *G01N 33/50* | (2006.01) | |
| *G01N 33/68* | (2006.01) | |

(52) U.S. Cl.
CPC .......... *A01K 67/0275* (2013.01); *C12Q 1/6883* (2013.01); *G01N 33/5023* (2013.01); *G01N 33/6872* (2013.01); *A01K 2227/105* (2013.01); *A01K 2267/03* (2013.01); *A01K 2267/0393* (2013.01); *C12Q 2600/106* (2013.01); *G01N 2800/14* (2013.01)

(58) Field of Classification Search
CPC ............. C12N 2503/02; C12Q 1/6897; A01K 2217/00; G01N 2800/14
See application file for complete search history.

(56) References Cited

U.S. PATENT DOCUMENTS

2005/0287127 A1* 12/2005 Li et al. ................ 424/93.21
2006/0024278 A1*  2/2006 Chen .................... 424/93.21
2006/0246446 A1* 11/2006 Evans et al. .............. 435/6

OTHER PUBLICATIONS

Kristen Radde-Gallwitz et al., Expression of Islet1 Marks the Sensory and Neuronal Lineages in the Mammalian Inner Ear. The Journal of Comparative Neurology 477:412-421 (2004).*
Lizhu Lin et al., Beta-Catenin directly regulates Islet1 expression in cardiovascular progenitors and is required for multiple aspects of cardiogenesis. PNAS, May 29, 2007, vol. 104, No. 22: 9313-9318.*
Li et al., Islet-1 Expression in the Developing Chicken Inner Ear. The Journal of Comparative Neurology 477:1-10 (2004).*
Sun et al., A central role for Islet1 in sensory neuron development linking sensory and spinal gene regulatory programs. Nature Neuroscience vol. 11, No. 11, p. 1283-1293, Nov. 2008.*
Cheng et al., Mechanisms of hair cell death and protection. Current Opinion in Otolaryngology & Head and Neck Surgery 2005, 13:343-348.*
Bielefeld et al., "Age-related hearing loss: Is it a preventable condition?" Hear Res., 264(1-2):98-107 (Epub 2009).
Cai et al., "Isl1 identifies a cardiac progenitor population that proliferates prior to differentiation and contributes a majority of cells to the heart," Dev. Cell., 5:877-889 (2003).
Edge et al., "Hair cell regeneration," Current Opinion in Neurobiology, 18(4):377-382 (2008).
Henry et al., "Genotypic differences in behavioral, physiological and anatomical expressions of age-related hearing loss in the laboratory mouse," Audiology 19:369-383 (1980).
Holley, "Keynote review: The auditory system, hearing loss and potential targets for drug development," Drug Discovery Today, 10(19):1269-1282 (2005).
Huang et al., "Diverse expression patterns of LIM-homeodomain transcription factors (LIM-HDs) in mammalian inner ear development," Dev. Dyn., 237:3305-3312 (2008).
International Search Report issued in PCT/US2010/039428 on Mar. 18, 2011.
Johnson et al., "A major gene affecting age-related hearing loss is common to at least ten inbred strains of mice," Genomics, 70:171-180 (2000).
Karlsson et al., "Insulin gene enhancer binding protein Isl-1 is a member of a novel class of proteins containing both a homeo- and a Cys-His domain," Nature, 344:879-882 (1990).
Kujawa et a., "Adding insult to injury: cochlear nerve degeneration after "temporary" noise-induced hearing loss," J. Neurosci., 29:14077-14085 (2009).
Laugwitz et al., "Islet1 cardiovascular progenitors: a single source for heart lineages?," Development, 135:193-205 (2008).
Le Prell et al., "Mechanisms of noise-induced hearing loss indicate multiple methods of prevention," Hear Res., 226:22-43 (2007).
Lee et al., "C-MYC and FGF Represent Two Distinct Mechanisms in Zebrafish Hair Cell Regeneration," in 7th Molecular Biology of Hearing and Deafness. 2009 (Abstract).
Liberman et al., "Effects of Selective Inner Hair Cell Loss on DPOAE and CAP in Carboplatin-Treated Chinchillas," Aud. Neursci., 3:255-268 (1997).
Lin et al, "Beta-catenin directly regulates Islet1 expression in cardiovascular progenitors and is required for multiple aspects of cardiogenesis," PNAS, 104(22):9313-9318 (2007).

(Continued)

*Primary Examiner* — Kevin Hill
*Assistant Examiner* — Arthur S Leonard
(74) *Attorney, Agent, or Firm* — Fish & Richardson P.C.

(57) ABSTRACT

Described are methods and compositions for increasing islet-1 (Isl1) activity (e.g., biological activity) and or expression (e.g., transcription and/or translation) in a biological cell and or in a subject.

22 Claims, 6 Drawing Sheets

(56) References Cited

OTHER PUBLICATIONS

Lin et al., "Isl1 is upstream of sonic hedgehog in a pathway required for cardiac morphogenesis," Dev. Biol., 295:756-763 (2006).

Mikuriya et al., "Attenuation of progressive hearing loss in a model of age-related hearing loss by a heat shock protein inducer, geranylgeranylacetone," Brain Res., 1212:9-17 (2008).

Mosser et al., "Use of a dicistronic expression cassette encoding the green fluorescent protein for the screening and selection of cells expressing inducible gene products," Bio Techniques, 22(1):150-161 (1997).

Mu et al., "Gene regulation logic in retinal ganglion cell development: Isl1 defines a critical branch distinct from but overlapping with Pou4f2," Proc. Natl. Acad. Sci. USA, 105:6942-6947 (2008).

Nagashima et al., "Transcriptional factors in the cochlea within the inner ear," Journal of Pharmacological Sciences, 99(4):301-306 (2005).

Pauley et al., "Stem cells and molecular strategies to restore hearing," Panminerva Medica, 50(1):41-53 (2008).

Pfaff et al, "Requirement for LIM homeobox gene Isl1 in motor neuron generation reveals a motor neuron-dependent step in interneuron differentiation," Cell, 84(2):309-320 (1996).

Radde-Gallwitz, "Expression of Islet1 marks the sensory and neuronal lineages in the mammalian inner ear," Journal of Comparative Neurology, 477(4):412-421 (2004).

Schuknecht, H. F., "Further Observations on the Pathology of Presbycusis," Arch. Otolaryngol., 80:369-382 (1964).

Spongr et al., "Quantitative measures of hair cell loss in CBA and C57BL/6 mice throughout their life spans," J. Acoust. Soc. Am., 101:3546-3553 (1997).

Sun et al., "A central role for Islet1 in sensory neuron development linking sensory and spinal gene regulatory programs," Nature Neuroscience, 11:1283-1293 (2008).

Trune et al., "Auditory function in the C3H/HeJ and C3H/HeSnJ mouse strains," Hear Res., 96:41-45 (1996).

Xiang et al., "Essential role of POU-domain factor Brn-3c in auditory and vestibular hair cell development," Proc. Natl. Acad. Sci. USA, 94:9445-9450 (1997).

\* cited by examiner

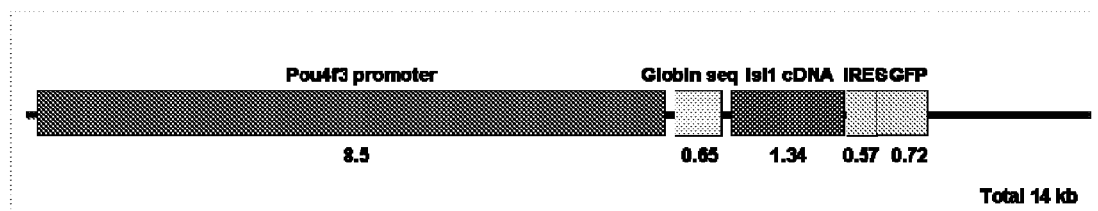
Figure 1
Figure 2A
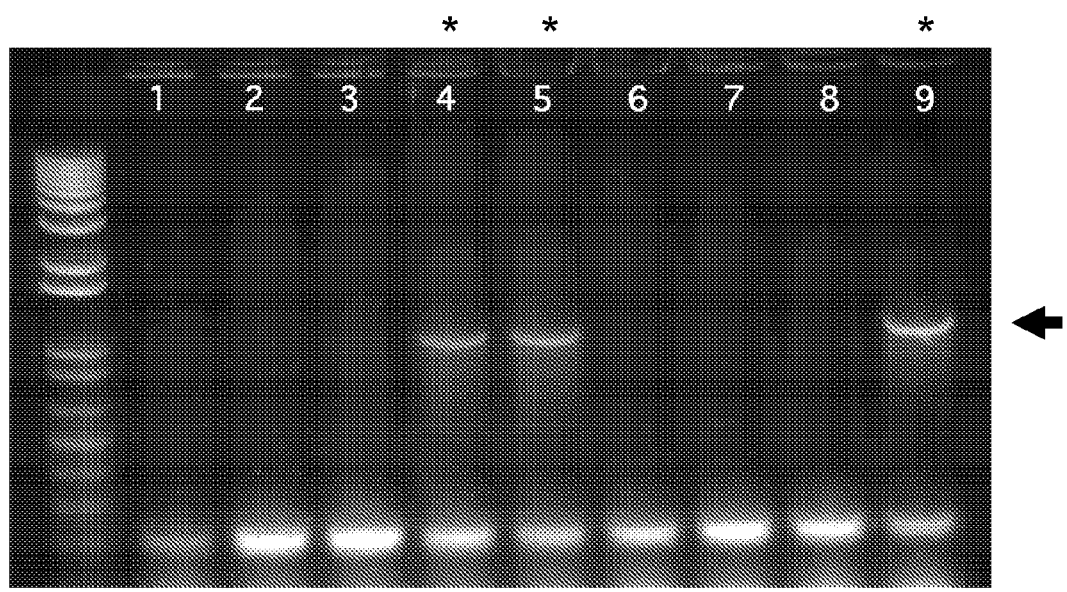
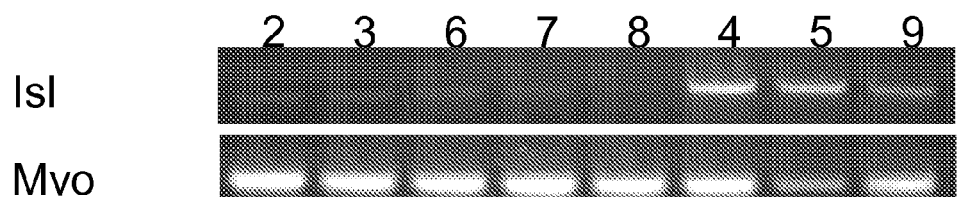
Figure 2B

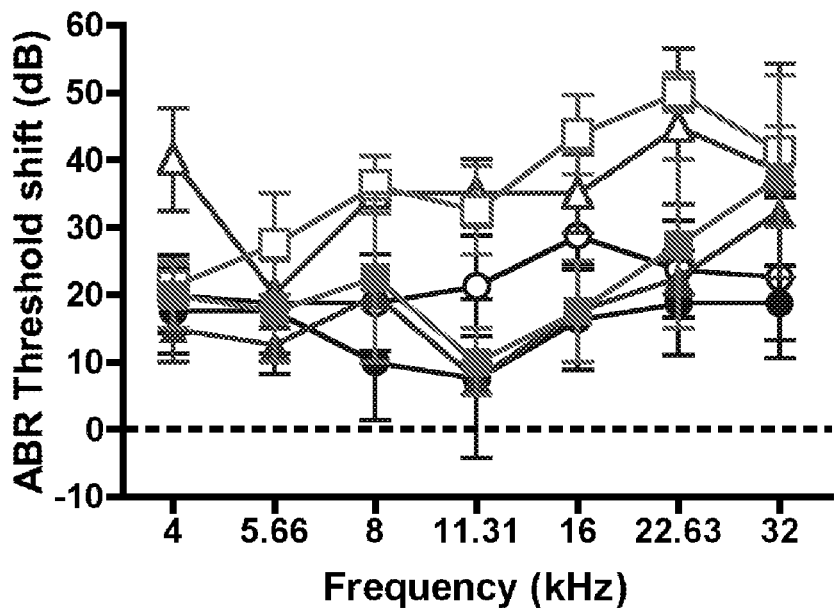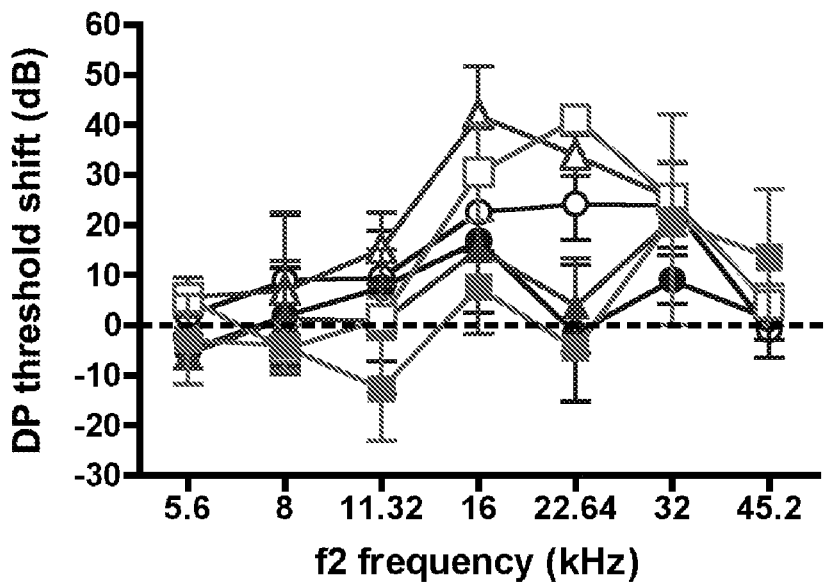

—○— WT-ctrl 1-wk post n=2
—●— Isl1-TG 1-wk post n=4
—□— WT-ctrl 2-wk post n=2
—▩— Isl1-TG 2-wk post n=4

ISLET1 (ISL1) AND HEARING LOSS

RELATED APPLICATIONS

This application is the U.S. National Stage of International Application No. PCT/US2010/039428, filed Jun. 22, 2010, and claims the benefit of U.S. Provisional Patent Application Ser. No. 61/219,248, filed on Jun. 22, 2009. The entire contents of the foregoing applications are hereby incorporated by reference.

STATEMENT REGARDING FEDERALLY SPONSORED RESEARCH OR DEVELOPMENT

This invention was made with government support under grant numbers DC006908 awarded by the National Institutes of Health. The government has certain rights in the invention.

TECHNICAL FIELD

This disclosure relates to methods and compositions for treating hearing loss and vestibular disorders in a subject.

BACKGROUND

More than 30 million people in the US suffer from hearing loss or vestibular disorders. One in three people older than 60 and one in two people older than 85 have some degree of age-related hearing loss (ARHL). With increased life expectancy, more people from each successive generation will likely suffer from hearing loss. Noise-induced inner ear damage/loss (NIHL) is also a major cause of hearing loss and vestibular disorders, which affects both young and aged populations. The cause of hearing loss, in particular age-related hearing loss (ARHL), is not well understood. As there is presently no effective treatment for hearing loss, hearing loss is a debilitating disorder causing heavy burden for individuals as well as the society. Novel strategies for the treatment of hearing loss and vestibular disorders are required.

SUMMARY

The present invention is based, in part, on the discovery that increasing islet-1 expression in ear hair cells in mice could protect the mice from hearing loss associated with aging or exposure to noise. Thus, provided herein are, inter alia, methods for treating hearing loss in a subject by increasing the expression (e.g., transcription and/or translation) or activity of islet-1 in ear hair cells in the subject and for identifying compounds for treating hearing loss.

In one aspect, provided herein are methods for identifying a candidate compound for treating age-related or noise-induced hearing loss, the method comprising: providing a test sample comprising a cell that expresses Isl1; contacting the test sample with a test compound; and detecting an expression or an activity of Isl1 in the cell; wherein an increase in the expression or the activity of Isl1 in the presence of the test compound as compared to in the absence of the test compound indicates that the test compound is a candidate compound for treating age-related or noise-induced hearing loss.

Also provided herein are method for identifying a candidate compound for treating age-related or noise-induced hearing loss, the method comprising: providing a test sample comprising a cell that expresses a reporter gene under the control of an Isl1 promoter; contacting the test sample with a test compound; and detecting an expression of the reporter gene in the cell; wherein an increase in the expression of the reporter gene in the presence of the test compound as compared to in the absence of the test compound indicates that the test compound is a candidate compound for treating age-related or noise-induced hearing loss.

In some embodiments, the screening methods further include selecting a test compound that increases the expression or the activity of Isl1 or the expression of the reporter gene in the cell; administering the test compound to a test animal; and detecting an expression of Isl1 in auditory hair cells of the test animal; wherein an increase in the expression of Isl1 in the auditory hair cells in the presence of the test compound as compared to in the absence of the test compound indicates that the test compound is a candidate compound for treating age-related or noise-induced hearing loss.

In one aspect, uses of a compound that increases expression of islet-1 (Isl1) for the treatment of age-related or noise-induced hearing loss in a subject are provided herein.

In another aspect, described herein are methods for treating age-related or noise-induced hearing loss in a subject, the method comprising: identifying a subject in need of such treatment; and administering to the subject an effective amount of an Isl1 modulating compound, e.g., a compound that increases expression of Isl1 in the subject.

In some embodiments, the Isl1 modulating compound, e.g., one that increases expression of Isl1, is administered systemically or to the inner ear of the subject. In some embodiments, the compound is an Isl1 nucleic acid or polypeptide. In some embodiments, the compound is a small molecule drug.

In some embodiments, the uses described herein further include the use of a compound that decreases expression or an activity of retinoblastoma protein (pRb).

The therapeutic methods provided herein can further comprise administering to the subject an effective amount of a compound that decreases expression or an activity of retinoblastoma protein (pRb).

In one aspect, described herein are transgenic mice whose auditory hair cells comprise an exogenous islet-1 (Isl1) gene under the control of a hair-cell specific promoter, wherein the Isl1 gene is overexpressed specifically in the auditory hair cells in the mouse.

In some embodiments, the hair-cell specific promoter is Pou4f3 promoter. In some embodiments, the auditory hair cells of the transgenic mice further comprise a reporter gene under the control of the hair-cell specific promoter.

Also included herein are auditory hair cells obtained from the transgenic mice of the present invention.

DEFINITIONS

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient that can be attributed to or associated with treatment by the compositions and methods of the present invention.

The terms "effective amount" and "effective to treat," as used herein, refer to an amount or a concentration of one or more compounds or a pharmaceutical composition described herein utilized for a period of time (including acute or chronic administration and periodic or continuous administration) that is effective for treating or preventing hearing loss.

Effective amounts of one or more compounds or a pharmaceutical composition for use in the present invention include amounts that treat a disease that would benefit from increased Isl1 expression, e.g., prevent or delay the onset, delay or halt the progression, ameliorate the effects of, or generally improve the prognosis of a subject diagnosed with one or more diseases that would benefit from increased Isl1 expression, e.g., one or more of the diseases described herein. For example, in the treatment of hearing impairment, a compound which improves hearing to any degree or delays or arrests any symptom of hearing impairment would be therapeutically effective. A therapeutically effective amount of a compound is not required to cure a disease but will provide a treatment for a disease.

The term "subject" is used throughout the specification to describe an animal, human or non-human, to whom treatment according to the methods of the present invention is provided. Veterinary and non-veterinary applications are contemplated. The term includes, but is not limited to, birds and mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

As used herein "target cell" and "target cells" refers to an auditory hair cell and/or a cell or cells that are capable of undergoing conversion (e.g., differentiation) to or towards a cell or cells that have one or more characteristics of auditory hair cells. Such target cells can include, but are not limited to, e.g., stem cells (e.g., inner ear stem cells, adult stem cells, bone marrow derived stem cells, embryonic stem cells, mesenchymal stem cells, skin stem cells, and fat derived stem cells), progenitor cells (e.g., inner ear progenitor cells), support cells (e.g., Deiters' cells, pillar cells, inner phalangeal cells, tectal cells and Hensen's cells), and/or germ cells. As described herein, prior to treatment with the methods, compounds, and compositions described herein, each of these target cells can be identified using a defined set of one or more markers (e.g., cell surface markers) that is unique to the target cell. A different set of one or more markers (e.g., cell surface markers) can also be used to identify target cells that have a partial or complete conversion (e.g., partial or complete differentiation) to or towards a cell that has characteristics of auditory hair cells or an auditory hair cell.

As used herein, "Isl1 modulating compounds" or simply "compounds" include any compound that can increase Isl1 levels (e.g., protein levels) and/or activity (e.g., biological activity) in target cells. Alternatively or in addition, the strategies can promote an increase in the levels (e.g. protein levels) and/or activity (e.g., biological activity) of Isl1 in the nucleus of target cells.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the invention will be apparent from the following detailed description and figures, and from the claims.

BRIEF DESCRIPTION OF THE DRAWINGS

FIG. 1 is a schematic diagram of an exemplary construct used to create Isl1-transgenenic mice (Isl1-TG).

FIG. 2A is an image of a gel showing the results of genotype analysis performed using standard methods, indicating the presence of the transgene.

FIG. 2B is an image of a gel showing the results of RT-PCR from utricle showed overexpression of Isl1 in Isl1-TG mice, with Myo7a as a control that normalizes mRNA from hair cells. The samples were the same as in FIG. 2A.

FIGS. 3A-D are line graphs showing the results of ABR and DPOAE tests performed at 3, 6, 8, 12 months. ABR (3A) and DPOAE (3B) thresholds of Isl1-TG and control (WT) mice were evaluated. ABR (3C) and DPOAE (3D) threshold shifts in the Isl1-TG and control mice were also calculated.

DETAILED DESCRIPTION

Figure 3A:
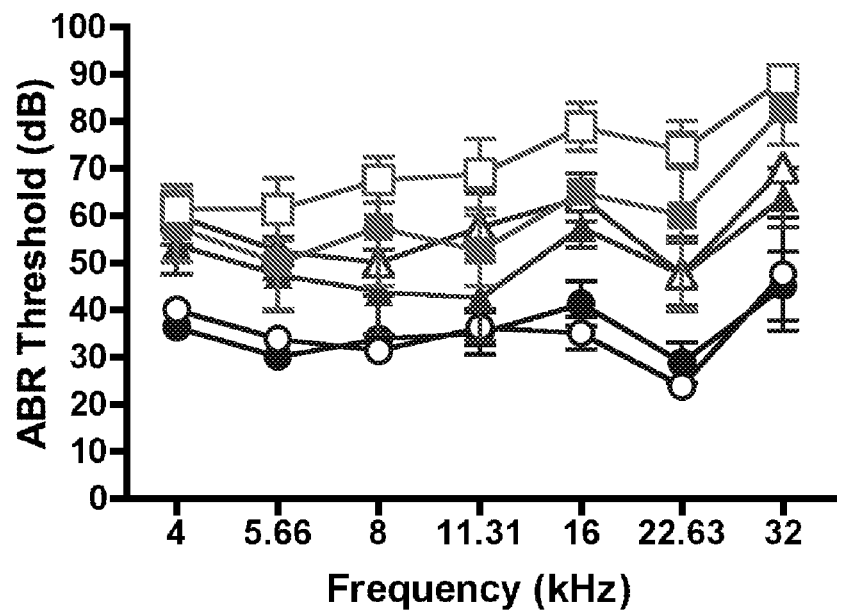
Figure 3B:
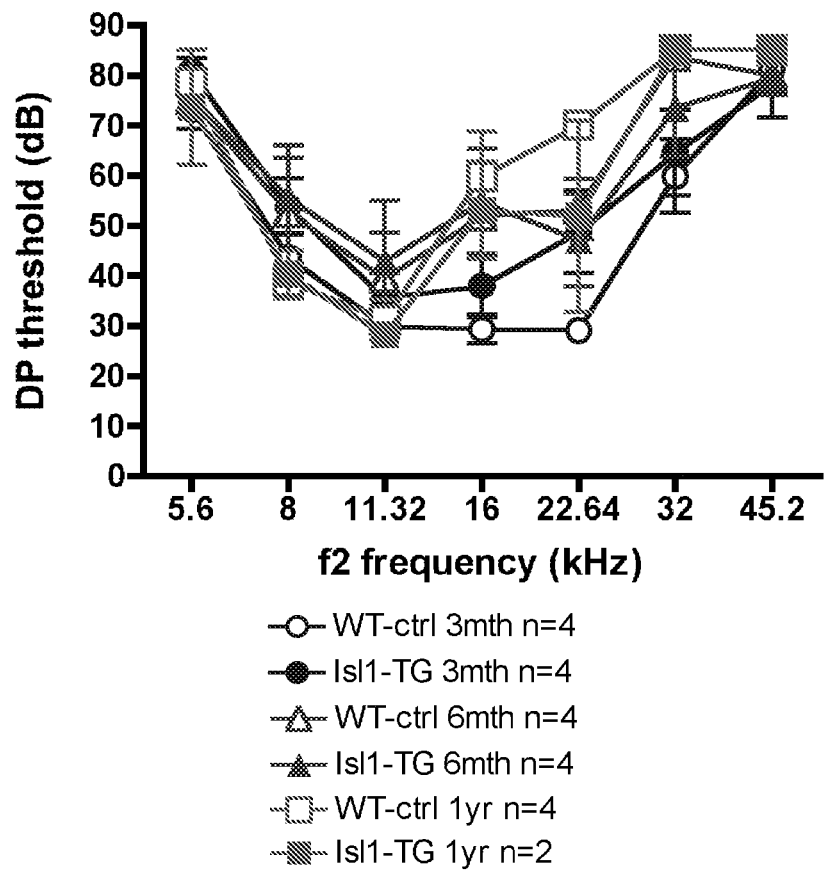

The present disclosure provides, inter alia, methods and pharmaceutical compositions for treating hearing loss and/or vestibular disorders in a subject. More specifically, the present disclosure provides methods and compositions for treating hearing loss in a subject by increasing the activity (e.g., biological activity) and/or expression (e.g., transcription and/or translation) of Isl1 in a cell, e.g., an auditory hair cell.

While the treatment methods are not limited to those in which particular underlying cellular events occur, the present compounds and compositions may increase the expression of an Isl1 gene in a subject and/or target cell.

The present disclosure is based, at least in part, on results generated using the Isl1 transgenic mouse model described herein. Briefly, the Isl1 transgenic mouse model (Isl1-TG) allows overexpression of the Isl1 transgene in postnatal mice under the control of the promoter of a hair cell specific transcription factor, Pou4f3, specifically in inner ear auditory hair cells in both the cochlea and vestibular system. Expression of the Isl1 transgene can be monitored using green fluorescent protein (see the Examples below).

Isl1-TG animals were less susceptible to age-related hearing loss (ARHL) and noise-induced hearing loss (NIHL), demonstrating that Isl1 can be used to promote auditory hair cell viability or health and protect against hair cell loss (see the Examples below). Accordingly, the present disclosure provides compositions and methods for reducing or protecting against auditory hair cell loss by increasing Isl1 expression in auditory hair cells or cells capable of differentiating into a cell with one or more characteristics of an auditory hair cell. The present disclosure also provides methods for identifying agents that increase Isl1 activity and/or expression using Isl1-TG animals or auditory hair cells obtained from (e.g., isolated and/or purified) Isl1-TG. Also provided are methods for identifying compounds for treating hearing loss associated with aging and noise. In addition, the present disclosure provides Isl1-TG as a biological tool to study the etiological events that lead to hearing loss and/or vestibular dysfunction.

Islet-1 (Isl1)

Islet-1 (Isl1) is a LIM-homeodomain transcription factor (LIM-HD) that is critical in the development and differentiation of the nervous system, such as the motor neurons. In addition, Isl1 controls pituitary and pancreas organogenesis, and is a key marker of cardiac progenitor cells. Functional studies using a conditional knockout model showed that Isl1 is also required for the development of retinal ganglion cells and forebrain cholinergic neurons.

Isl1 is expressed in the prosensory region of otocyst, and is subsequently expressed in early supporting cells and hair cells. Isl1 expression in hair cells is downregulated during later differentiation. In hair cells, expression of transcription factor of Pou4f3 leads to Lhx3 expression, which in turn suppresses Isl1 expression. This is confirmed by the lack of Lhx3 expression in the Pou4f3-null hair cells, and by overexpression of Lhx3 in cochlea nonsensory cells, which leads to Isl1 suppression.

Isl1 is known to be involved in motor neuron specification (Pfaff et al., Cell, 84(2):309-320 (1996)). Isl1 positive cells have also been identified in adult heart stem cells (Laugwitz et al., Development 135:193-205 (2008)).

The developmental role of Isl1 has also been reported. Isl1 is normally expressed in early inner ear development, suggesting a role in progenitor cell specification. Isl1 is not expressed in the cochlea, including auditory hair cells and supporting cells, in postnatal mice. In the postnatal utricle, Isl1 expression is expressed weakly in the supporting cells but not hair cells.

As used herein, "Isl1" refers to any and all Isl1-associated nucleic acid or protein sequences and includes any sequence that is orthologous or homologous to, or has significant sequence similarity to, an Isl1 nucleic acid or amino acid sequence derived from any animal including mammals (e.g., humans) and insects. Isl1 also includes all other synonyms that may be used to refer to this gene or the protein product of this gene (synonyms for this gene include ISL LIM homeobox 1, ISL1 transcription factor, LIM/homeodomain 2, ISL1 transcription factor, LIM/homeodomain, and islet-1).

Isl1 polypeptides are, e.g., 349 amino acids in length and about 39 kDa. The chromosomal loci of Isl1 is 5q11.2. Human Isl1 sequences can be found in GenBank at Acc. No. NC_000005.9 (genomic), NT_006713.15 (genomic), NM_002202.2 (mRNA), and NP_002193.2 (protein). Antibodies that can be used to detect an Isl1 polypeptide are commercially available, e.g., from Cell Signaling Technology, Abcam, Novus Biologicals, Sigma-Aldrich, R&D Systems, Millipore, Abnova, and/or Invitrogen).

Methods of Treatment

In some embodiments, the present disclosure provides novel therapeutic strategies for treating diseases that would benefit from an increase in Isl1 expression and/or activity, e.g., hearing loss, e.g., NIHL or ARHL. In some embodiments, such strategies can promote an increase in the levels (e.g., protein levels) and/or activity (e.g., biological activity) of Isl1 in target cells. In other embodiments, downstream target genes or proteins of Isl1 in hair cells may be modulated to treat NIHL or ARHL.

In some embodiments, the present disclosure provides methods whereby:

(a) one or more Isl1 modulating compounds are administered to a subject, e.g., to the ear of a subject (direct therapy);

(b) one or more target cells are contacted, e.g., in vitro, with one or more Isl1 modulating compounds, and administered to a subject, e.g., to the ear of a subject (cell therapy); and (c) a combination of (a) and (b) (combination therapy).

Increasing the level or activity of other inner ear progenitor genes in hair cells, e.g., Sox2 and Prox1, may also treat NIHL or ARHL.

Compositions and Methods for Modulating Isl1 Expression

In some embodiments, the present disclosure includes the use of compounds, compositions (referred to collectively herein as Isl1 modulating compounds) and methods that increase the levels (e.g., protein levels) and/or activity (e.g., biological activity) of Isl1 in target cells.

(i) Isl1 Nucleic Acid Expression Constructs

In some embodiments, the Isl1 modulating agent is a gene or nucleic acid comprising a Isl1 nucleic acid sequence. Any Isl1 gene or nucleic acid sequence can be expressed, e.g., in one or more auditory hair cells, using one or more expression constructs. Exemplary Isl1 nucleic acid sequences that may be usefully expressed include, but are not limited to, for example, nucleic acid sequences such as National Center for Biotechnology Information (NCBI) accession numbers NM_002202.2 (human Isl1 mRNA), BC031213.1 (human Isl1 cDNA), NM_021459.4 (murine Isl1 mRNA), BC132609.1 (murine Isl1 cDNA), and BC132263.1 (murine Isl1 cDNA), and any nucleic acid sequence with at least 50% (e.g., 60%, 70%, 80%, 85%, 90%, 95%, 98%, 99%, or 100%) sequence identity to NCBI accession numbers NM_002202.2, BC031213.1, NM_021459.4, BC132609.1, and BC132263.1. In some embodiments, Isl1 nucleic acid can include nucleic acid encoding an Isl1 polypeptide such as NCBI accession numbers EAW54861.1, NP_002193.2, P63171.1, NP_067434.3, AAI46164.1, AAI32264.1, ABM85672.1, EDM10395.1, ABM82484.1, EDL18368.1, and EDL18367.1, and any amino acid sequence with at least 50% (e.g., 60%, 70%, 80%, 85%, 90%, 95%, 98%, 99%, or 100%) sequence identity to NCBI accession numbers EAW54861.1, NP_002193.2, P63171.1, NP_067434.3, AAI46164.1, AAI32264.1, ABM85672.1, EDM10395.1, ABM82484.1, EDL18368.1, and EDL18367.1.

In some embodiments, DNA encoding Isl1 can be an unmodified wild type sequence. Alternatively, DNA encoding Isl1 can be modified using standard molecular biological techniques. For example, DNA encoding Isl1 can be altered or mutated, e.g., to increase the stability of the DNA or resulting polypeptide. Polypeptides resulting from such altered DNAs will retain the biological activity of wild type Isl1. In some embodiments, DNA encoding Isl1 can be altered to increase nuclear translocation of the resulting polypeptide. In some embodiments, DNA encoding Isl1 can be modified using standard molecular biological techniques to include an additional DNA sequence that can encode one or more of, e.g., detectable polypeptides, signal peptides, and protease cleavage sites.

In some embodiments, the nucleic acids described herein, e.g., nucleic acids encoding an Isl1 polypeptide or active fragment thereof, or a nucleic acid encoding a protein that increases Isl1 expression, level or activity, can be incorporated into a gene construct to be used as a part of a gene therapy protocol. The invention includes targeted expression vectors for in vivo transfection and expression of a polynucleotide that encodes an Isl1 polypeptide or active fragment thereof, or a protein that increases Isl1 expression, level, or activity as described herein, in particular cell types (e.g., auditory hair cells or cells with, or that are capable of differentiating into a cell with, one or more characteristics of an auditory hair cell). Such expression constructs can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, poxvirus, alphavirus, and herpes simplex virus-1, or recombinant bacterial or eukaryotic plasmids. Viral vectors transfect cells directly; plasmid DNA can be delivered naked or with the help of, for example, cationic liposomes (e.g., LIPOFECTAMINE) or derivatized (e.g., antibody conjugated), polylysine conjugates, gramicidin S, artificial viral envelopes or other such intracellular carriers, as well as direct injection of the gene construct or $CaPO_4$ precipitation carried out in vivo.

One approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (Reviewed in Hu and Pathak, Pharmacol. Rev. 52: 493-511 (2000); Young et al., J. Pathol. 208:229-318 (2006)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel et al. (eds.), 2002, "Short Protocols in Molecular Biology," John Wiley & Sons, Inc., and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2, ΨAm, pA12 and PA317 (For a review, see Miller et. al, Hum. Gene Ther. 1:5-14 (1990)). Retroviruses have been used to introduce a variety of genes into many different cell types, including epithelial cells, in vitro and/or in vivo (see for example Eglitis et al., Science 230:1395-1398 (1985); Danos and Mulligan, Proc. Natl. Acad. Sci. USA 85:6460-6464 (1988); Wilson et al., Proc. Natl. Acad. Sci. USA 85:3014-3018 (1988); Armentano et al., Proc. Natl. Acad. Sci. USA 87:6141-6145 (1990); Miller et al., Blood 76:271-8 (1990); Huber et al. Proc. Natl. Acad. Sci. USA 88:8039-8043 (1991); Ferry et al. Proc. Natl. Acad. Sci. USA 88:8377-8381 (1991); Chowdhury et al. Science 254:1802-1805 (1991); van Beusechem et al. Proc. Natl. Acad. Sci. USA 89:7640-7644 (1992); Kay et al. Human Gene Therapy 3:641-647 (1992); Dai et al. Proc. Natl. Acad. Sci. USA 89:10892-10895 (1992); Hwu et al. J. Immunol. 150:4104-4115 (1993); Cavazzana-Calvo et al., Science 288:669-672 (2000); U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The generation of replication-deficient adenovirus was achieved through the manipulation of the genome of an adenovirus, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases (kb)) relative to other gene delivery vectors (Berkner et al., supra; Haj-Ahmand and Graham, J. Virol. 57:267 (1986). Additionally, special high-capacity adenoviral (HC-Ad) vectors have been created that can contain more than 30 kb of transgene (Kochanek et al., Hum. Gene Ther. 10:2451-9 (1999)).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle (Reviewed in McCarty et al., Annu Rev Genet 38:819-45 (2004); Daya et al., Clin. Microbiol. Rev. 21: 583-93 (2008)). It is also one of the few viruses that may integrate its DNA into non-dividing cells, and exhibits a high frequency of stable integration that can lead to long term expression (see for example Samulski et al., J. Virol. 63:3822-3828 (1989); and McLaughlin et al., J. Virol. 62:1963-1973 (1989); Flotte et al., Am. J. Respir. Cell. Mol. Biol. 7:349-356 (1992); Miller et al., Nature Genet. 36:767-773 (2004)). Vectors containing as little as 300 base pairs of AAV can be packaged and can integrate. Space for exogenous DNA is limited to about 4 kb. An AAV vector such as that described in Tratschin et al., Mol. Cell. Biol. 5:3251-3260 (1985) can be used to introduce DNA into cells. Through the use of AAV vectors, which are derived from many different serotypes, a variety of nucleic acids have been introduced into different cell types (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993); Summerford et al., J. Virol. 72:1438-45 (1998); Davidson et al., Proc. Natl. Acad. Sci. USA 97:3428-32 (2000); Zabner et al., J. Virol. 74:3852-8 (2000); Rabinowitz J E et al., J. Virol. 76:791-801 (2002); Davidoff et al., Mol Ther. 11:875-88 (2005); Mueller et al., Gene Ther. 15:858-63. (2008)).

In addition to viral transfer methods, such as those illustrated above, non-viral methods can also be employed to cause expression of a nucleic acid compound described herein (e.g., a polypeptide encoding ISL1 nucleic acid or a polypeptide encoding a compound that increases ISL1 expression, levels or activity) in the tissue of a subject (For a review see Niidome et al., Gene Ther. 9:1647-52 (2002)). Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-cationic conjugates such as polyamine and polylysine, and artificial viral envelopes. Other embodiments include plasmid injection systems such as are described in Cohen et al., Gene Ther. 7:1896-905 (2000); Tam et al., Gene Ther. 7:1867-74 (2000); Meuli et al., J. Invest. Dermatol. 116:131-135 (2001); or Fenske et al., Methods Enzymol. 346:36-71 (2002).

In some embodiments, a gene encoding a compound described herein, e.g., ISL1 or a compound modulating Isl1 expression, level or activity, is entrapped in liposomes bearing positive charges on their surface (e.g., lipofectins), which can be tagged with an adaptor molecule, such as biotin or antibodies against cell surface antigens of the target tissue, to facilitate targeting (Mizuno et al., No Shinkei Geka 20:547-551 (1992); Bartlett et al., Nat. Biotechnol. 17:181-6 (1999); Arnold et al., Mol. Ther. 14:97-106 (2006); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art or is described herein. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

In some aspects, Isl1 can be expressed using expression constructs, e.g., naked DNA constructs, DNA vector based constructs, and/or viral vector and/or viral based constructs.

Naked DNA constructs and the therapeutic use of such constructs are well known to those of skill in the art (see, e.g., Chiarella et al., Recent Patents Anti-Infect. Drug Disc., 3:93-101, 2008; Gray et al., Expert Opin. Biol. Ther., 8:911-922, 2008; Melman et al., Hum. Gene Ther., 17:1165-1176, 2008). In some embodiments, naked DNA constructs include one or more therapeutic nucleic acids (e.g., DNA encoding Isl) and a promoter sequence. A naked DNA construct can be a DNA vector, commonly referred to as pDNA. Naked DNA typically do not incorporate into chromosomal DNA. Generally, naked DNA constructs do not require, or are not used in conjunction with, the presence of lipids, polymers, or viral proteins. Such constructs may also include one or more of the non-therapeutic components described herein.

DNA vectors are known in the art and typically are circular double stranded DNA molecules. DNA vectors usually range in size from three to five kilo-base pairs (e.g., including inserted therapeutic nucleic acids). Like naked DNA, DNA vectors can be used to deliver and express one or more therapeutic proteins in target cells. DNA vectors do not incorporate into chromosomal DNA.

Generally, DNA vectors include at least one promoter sequence that allows for replication in a target cell. Uptake of a DNA vector may be facilitated (e.g., improved) by combining the DNA vector with, for example, a cationic lipid, and forming a DNA complex.

In some embodiments, DNA vectors can be introduced into target cells via conventional transformation or transfection techniques. As used herein, the terms "transformation" and "transfection" are intended to refer to a variety of art-recognized techniques for introducing foreign nucleic acid (e.g., DNA) into a target cell, including calcium phosphate or calcium chloride co-precipitation, DEAE-dextran-mediated transfection, lipofection, or electroporation.

The present application also provides such expression constructs formulated as a pharmaceutical composition, e.g., for administration to a subject. Such pharmaceutical compositions are not limited to one expression construct and rather can include two or more expression constructs (e.g., two, three, four, five, six, seven, eight, nine, ten or more expression constructs).

All the molecular biological techniques required to generate an expression construct described herein are standard techniques that will be appreciated by one of skill in the art. Detailed methods may also be found, e.g., *Current Protocols in Molecular Biology*, Ausubel et al. (eds.) Greene Publishing Associates, (1989), Sections 9.10-9.14 and other standard laboratory manuals. DNA encoding altered ISL1 can be generated using, e.g., site directed mutagenesis techniques.

(ii) Isl1 Polypeptides and Proteins

In some embodiments, the Isl1 modulating agent is an Isl1 polypeptide. Exemplary useful Isl1 polypeptides include, but are not limited to, for example, GenBank Acc. Nos. EAW54861.1, NP_002193.2, P63171.1, NP_067434.3, AAI46164.1, AAI32264.1, ABM85672.1, EDM10395.1, ABM82484.1, EDL18368.1, and EDL18367.1, and any amino acid sequence with at least 50% (e.g., 60%, 70%, 80%, 85%, 90%, 95%, 98%, 99%, or 100%) sequence identity to NCBI accession numbers EAW54861.1, NP_002193.2, P63171.1, NP_067434.3, AAI46164.1, AAI32264.1, ABM85672.1, EDM10395.1, ABM82484.1, EDL18368.1, and EDL18367.1.

Isl1 polypeptides can be generated using recombinant techniques or using chemical synthesis. Methods for generating such polypeptides, and methods required for the purification of such polypeptides, are known in the art, see, e.g., Sambrook, *Molecular Cloning: A Laboratory Manual* (CSHL Press, 3rtd Edition, 2001).

Modifications can be made to a protein to alter the pharmacokinetic properties of the protein to make it more suitable for use in protein therapy. For example, such modifications can result in longer circulatory half-life, an increase in cellular uptake, improved distribution to targeted tissues, a decrease in clearance and/or a decrease of immunogenicity. A number of approaches useful to optimize the therapeutic activity of a protein, e.g., a therapeutic protein described herein, e.g., a Isl1 modulating agent, a Isl1 polypeptide, peptide or peptide mimetic, a Isl1 analog are known in the art, including chemical modification.

Expression Systems

For recombinant proteins, the choice of expression system can influence pharmacokinetic characteristics. Differences in post-translational processing between expression systems can lead to recombinant proteins of varying molecular size and charge, which can affect circulatory half-life, rate of clearance and immunogenicity, for example. The pharmacokinetic properties of the protein may be optimized by the appropriate selection of an expression system, such as selection of a bacterial, viral, or mammalian expression system. Exemplary mammalian cell lines useful in expression systems for therapeutic proteins are Chinese hamster ovary, (CHO) cells, the monkey COS-1 cell line and the CV-1 cell line.

The recombinant expression vectors of the invention can be designed for expression of Isl1 polypeptides in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology*, 185, (Academic Press, San Diego, Calif. 1990). Alternatively, the recombinant expression vector can be transcribed and translated in vitro, for example using T7 promoter regulatory sequences and T7 polymerase.

Chemical Modification

A protein can be chemically altered to enhance the pharmacokinetic properties, while maintaining activity. The protein can be covalently linked to a variety of moieties, altering the molecular size and charge of the protein and consequently its pharmacokinetic characteristics. The moieties are preferably non-toxic and biocompatible. In one embodiment, polyethylene glycol (PEG) can be covalently attached to the protein (PEGylation). A variety of PEG molecules are known and/or commercially available (See, e.g., Sigma-Aldrich catalog). PEGylation can increase the stability of the protein, decrease immunogenicity by steric masking of epitopes, and improve half-life by decreasing glomerular filtration. (See, e.g., Harris and Zalipsky, Poly(ethylene glycol): Chemistry and Biological Applications, ACS Symposium Series, No. 680, American Chemical Society (1997); Harris et al., Clinical Pharmacokinetics, 40: 485-563, 2001). Examples of therapeutic proteins administered as PEG constructs include Adagen™ (PEG-ADA) and Oncospar™ (Pegylated asparaginase). In another embodiment, the protein can be similarly linked to oxidized dextrans via an amino group. (See Sheffield, Curr. Drug Targets Cardiovas. Haemat. Dis., 1:1-22, 2001). In yet another embodiment, conjugation of arginine oligomers to cyclosporin A can facilitates topical delivery (Rothbard et al., Nat. Med., 6: 1253-1257, 2000).

Furthermore, the protein can be chemically linked to another protein, e.g., cross-linked (via a bifunctional cross-linking reagent, for example) to a carrier protein to form a larger molecular weight complex with longer circulatory half-life and improved cellular uptake. In some embodiments, the carrier protein can be a serum protein, such as albumin. In another embodiment, the therapeutic protein can cross-link with itself to form a homodimer, a trimer, or a higher analog, e.g., via heterobifunctional or homobifunctional cross-linking reagents (see Stykowski et al., Proc. Natl. Acad. Sci. USA, 95:1184-1188, 1998). Increasing the molecular weight and size of the therapeutic protein through dimerization or trimerization can decrease clearance.

Modification of Protein Formulation

The formulation of the protein may also be changed. For example, the therapeutic protein can be formulated in a carrier system. The carrier can be a colloidal system. The colloidal system can be a liposome, a phospholipid bilayer vehicle. In one embodiment, the therapeutic protein is encapsulated in a liposome while maintaining protein integrity. As one skilled in the art would appreciate, there are a variety of methods to prepare liposomes. (See Lichtenberg et al., Methods Biochem. Anal., 33:337-462, 1988; Anselem et al., Liposome Technology, CRC Press (1993)). Liposomal formulations can delay clearance and increase cellular uptake (See Reddy, Ann. Pharmacother., 34:915-923, 2000).

In some embodiments, the fusion protein includes a cell-penetrating peptide sequence that facilitates delivery of Isl1 to the intracellular space, e.g., HIV-derived TAT peptide, penetratins, transportans, or hCT derived cell-penetrating peptides, see, e.g., Caron et al., Mol Ther. 3:310-8, 2001; Langel, *Cell-Penetrating Peptides: Processes and Applications* (CRC Press, Boca Raton Fla. 2002); El-Andaloussi et al., Curr. Pharm. Des., 11:3597-611, 2005; and Deshayes et al., Cell. Mol. Life Sci., 62:1839-49, 2005.

Peptide Mimetics

In some embodiments, the Isl1 modulating agent is a peptide mimetic (e.g., either a peptide or nonpeptide peptide mimetic). Synthesis of nonpeptide compounds that mimic peptide sequences (e.g., an Isl1 polypeptide sequence disclosed herein) are known in the art.

Methods for creating a peptidomimetic include substituting one or more, e.g., all, of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N-terminus to the C-terminus of the original peptide becomes the order of amino acid residues from the C-terminus to the N-terminus in the modified peptidomimetic. Such sequences can be referred to as "inverso" sequences. Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, i.e., an artificial amino acid analog. Artificial amino acid analogs include $\beta$-amino acids, $\beta$-substituted $\beta$-amino acids ("$\beta^3$-amino acids"), phosphorous analogs of amino acids, such as $\alpha$-amino phosphonic acids and $\alpha$-amino phosphinic acids, and amino acids having non-peptide linkages. Artificial amino acids can be used to create peptidomimetics, such as peptoid oligomers (e.g., peptoid amide or ester analogues), $\beta$-peptides, cyclic peptides, oligourea or oligocarbamate peptides; or heterocyclic ring molecules. These sequences can be modified, e.g., by biotinylation of the amino terminus and amidation of the carboxy terminus In some embodiments, the mimetics of the present disclosure are peptides having sequence homology to the herein-described Isl1 polypeptides. These mimetics include, but are not limited to, peptides in which L-amino acids are replaced by their D-isomers. One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant (Pearson and Lipman, Proc. Natl. Acad. Sci. (USA), 85:2444-2448, 1988;

Lipman and Pearson, Science, 227:1435-1441, 1985. More generally, the peptide ligands described herein and the mimetics described above can be synthesized using any known methods, including tea-bag methodology or solid phase peptide synthesis procedures described by Merrifield et al., Biochemistry, 21:5020-5031, 1982; Houghten Wellings, Proc. Natl. Acad. Sci. (USA), 82:5131-5135, 1985; Atherton, Methods in Enzymology, 289:44-66, 1997, or Guy and Fields, Methods in Enzymology, 289:67-83, 1997, or using a commercially available automated synthesizer.

In some embodiments, any of the peptides and peptide mimetics described herein can further include a heterologous polypeptide. The heterologous polypeptide can be a polypeptide that increases the circulating half-life of the peptide to which it is attached (e.g., fused, as in a fusion protein). The heterologous polypeptide can be an albumin (e.g., a human serum albumin or a portion thereof) or a portion of an immunoglobulin (e.g., the Fc region of an IgG).

Targeted Peptides

In some embodiments, an Isl1 modulating agent is a polypeptide that is targeted to an auditory hair cell or a cell with, or that is capable of differentiating into a cell with, one or more characteristics of an auditory hair cell. Alternatively or in addition, an Isl1 targeted peptide can be targeted to a specific tissue or organ, e.g., the inner ear (e.g., the cochlear).

Methods for targeting peptides against specific cell types and tissues are known in the art. For example, compositions and methods for targeting peptides and other therapeutic agents disclosed herein to specific cell or tissues include the use of materials that can target antigens or markers that are unique or specific to the intended target cell or tissue, for example, including but not limited to, antibodies or antigen binding fragments of antibodies, and short affinity peptides. In some embodiments, such materials will (1) be highly specific for a auditory hair cell marker, and/or (2), have a high affinity for the molecular target.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997). Useful Isl1 encoding polypeptide sequences or polypeptide fragments can have up to about 20 (e.g., up to about 10, 5, or 3) amino acid deletions, additions, or substitutions, such as conservative substitutions, to be useful for the compositions and methods described herein. Conservative amino acid substitutions are known in the art.

Nanoparticles

In some embodiments, an Isl1 modulating agent can be targeted to a specific tissue or organ using a nanoparticle. The nanoparticles useful in the methods and compositions described herein are made of materials that are (i) biocompatible, i.e., do not cause a significant adverse reaction in a living animal when used in pharmaceutically relevant amounts; (ii) feature functional groups to which the binding moiety can be covalently attached, (iii) exhibit low non-specific binding of interactive moieties to the nanoparticle, and (iv) are stable in solution, i.e., the nanoparticles do not precipitate. The nanoparticles can be monodisperse (a single crystal of a material, e.g., a metal, per nanoparticle) or polydisperse (a plurality of crystals, e.g., 2, 3, or 4, per nanoparticle).

A number of biocompatible nanoparticles are known in the art, e.g., organic or inorganic nanoparticles. Liposomes, dendrimers, carbon nanomaterials and polymeric micelles are examples of organic nanoparticles. Quantum dots can also be used. Inorganic nanoparticles include metallic nanoparticle, e.g., Au, Ni, Pt and TiO2 nanoparticles. Magnetic nanoparticles can also be used, e.g., spherical nanocrystals of 10-20 nm with a $Fe^{2+}$ and/or $Fe^{3+}$ core surrounded by dextran or PEG molecules. In some embodiments, colloidal gold nanoparticles are used, e.g., as described in Qian et al., Nat. Biotechnol. 26(1):83-90 (2008); U.S. Pat. Nos. 7,060,121; 7,232,474; and U.S. P.G. Pub. No. 2008/0166706. Suitable nanoparticles, and methods for constructing and using multifunctional nanoparticles, are discussed in e.g., Sanvicens and Marco, Trends Biotech., 26: 425-433 (2008).

In all embodiments, the nanoparticles are attached (linked) to the Isl1 modulating agent via a functional groups. In some embodiments, the nanoparticles are associated with a polymer that includes the functional groups, and also serves to keep the metal oxides dispersed from each other. The polymer can be a synthetic polymer, such as, but not limited to, polyethylene glycol or silane, natural polymers, or derivatives of either synthetic or natural polymers or a combination of these. Useful polymers are hydrophilic. In some embodiments, the polymer "coating" is not a continuous film around the magnetic metal oxide, but is a "mesh" or "cloud" of extended polymer chains attached to and surrounding the metal oxide. The polymer can comprise polysaccharides and derivatives, including dextran, pullanan, carboxydextran, carboxmethyl dextran, and/or reduced carboxymethyl dextran. The metal oxide can be a collection of one or more crystals that contact each other, or that are individually entrapped or surrounded by the polymer.

In other embodiments, the nanoparticles are associated with non-polymeric functional group compositions. Methods are known to synthesize stabilized, functionalized nanoparticles without associated polymers, which are also within the scope of this invention. Such methods are described, for example, in Halbreich et al., Biochimie, 80:379-90, 1998.

In some embodiments, the nanoparticles have an overall size of less than about 1-100 nm, e.g., about 25-75 nm, e.g., about 40-60 nm, or about 50-60 nm in diameter. The polymer component in some embodiments can be in the form of a coating, e.g., about 5 to 20 nm thick or more. The overall size of the nanoparticles is about 15 to 200 nm, e.g., about 20 to 100 nm, about 40 to 60 nm; or about 60 nm.

Synthesis of Nanoparticles

There are varieties of ways that the nanoparticles can be prepared, but in all methods, the result must be a nanoparticle with functional groups that can be used to link the nanoparticle to the binding moiety. For example, nanoparticles can be synthesized according to a version of the method of Albrecht et al., Biochimie, 80: 379-90, 1998. Dimercapto-succinic acid is coupled to the nanoparticle and provides a carboxyl functional group.

In another embodiment, the Isl1 modulating agents (e.g., Isl1 polypeptides) are attached to the nanoparticles via a functionalized polymer associated with the nanoparticle. In some embodiments, the polymer is hydrophilic. In a specific embodiment, the conjugates are made using oligonucleotides that have terminal amino, sulfhydryl, or phosphate groups, and superparamagnetic iron oxide nanoparticles bearing amino or carboxy groups on a hydrophilic polymer. There are several methods for synthesizing carboxy and amino derivatized-nanoparticles. Methods for synthesizing functionalized, coated nanoparticles are discussed in further detail below.

Carboxy functionalized nanoparticles can be made, for example, according to the method of Gorman (see WO 00/61191). Carboxy-functionalized nanoparticles can also be made from polysaccharide coated nanoparticles by reaction with bromo or chloroacetic acid in strong base to attach carboxyl groups. In addition, carboxy-functionalized particles can be made from amino-functionalized nanoparticles by converting amino to carboxy groups by the use of reagents such as succinic anhydride or maleic anhydride.

Nanoparticle size can be controlled by adjusting reaction conditions, for example, by varying temperature as described in U.S. Pat. No. 5,262,176. Uniform particle size materials can also be made by fractionating the particles using centrifugation, ultrafiltration, or gel filtration, as described, for example in U.S. Pat. No. 5,492,814.

Nanoparticles can also be treated with periodate to form aldehyde groups. The aldehyde-containing nanoparticles can then be reacted with a diamine (e.g., ethylene diamine or hexanediamine), which will form a Schiff base, followed by reduction with sodium borohydride or sodium cyanoborohydride.

Dextran-coated nanoparticles can also be made and crosslinked, e.g., with epichlorohydrin. The addition of ammonia will react with epoxy groups to generate amine groups, (see Hogemann et al., Bioconjug. Chem. 11:941-6, 2000; and Josephson et al., Bioconjug. Chem., 10:186-91, 1999).

Carboxy-functionalized nanoparticles can be converted to amino-functionalized magnetic particles by the use of water-soluble carbodiimides and diamines such as ethylene diamine or hexane diamine Avidin or streptavidin can be attached to nanoparticles for use with a biotinylated binding moiety, such as an oligonucleotide or polypeptide. See e.g., Shen et al., Bioconjug. Chem., 7:311-6, 1996. Similarly, biotin can be attached to a nanoparticle for use with an avidin-labeled binding moiety.

In all of these methods, low molecular weight compounds can be separated from the nanoparticles by ultra-filtration, dialysis, magnetic separation, or other means.

In some embodiments, colloidal gold nanoparticles are made using methods known in the art, e.g., as described in Qian et al., Nat. Biotechnol. 26:83-90, 2008; U.S. Pat. Nos. 7,060,121; 7,232,474; and U.S. P.G. Pub. No. 2008/0166706.

In some embodiments, the nanoparticles are pegylated, e.g., as described in U.S. Pat. Nos. 7,291,598; 5,145,684; 6,270,806; 7,348,030, and others.

(iii) Isl1 Antibodies

In some embodiments, an Isl1 modulating agent can be an antibody that increases the activity or expression of Isl1. The term "antibody," as used herein, refers to full-length, two-chain immunoglobulin molecules and antigen-binding portions and fragments thereof, including synthetic variants. A typical full-length antibody includes two heavy (H) chain variable regions (abbreviated herein as VH), and two light (L) chain variable regions (abbreviated herein as VL). The term "antigen-binding fragment" of an antibody, as used herein, refers to one or more fragments of a full-length antibody that retain the ability to specifically bind to a target. Examples of antigen-binding fragments include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546 (1989)), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. Science 242:423-426, 1988; and Huston et al. Proc. Natl. Acad. Sci. USA 85:5879-5883, 1988). Such single chain antibodies are also encompassed within the term "antigen-binding fragment."

Production of antibodies and antibody fragments is well documented in the field. See, e.g., Harlow and Lane, 1988. *Antibodies, A Laboratory Manual*. Cold Spring Harbor, N.Y.: Cold Spring Harbor Laboratory. For example, Jones et al., Nature 321: 522-525, 1986, which discloses replacing the CDRs of a human antibody with those from a mouse antibody. Marx, Science 229:455-456, 1985, discusses chimeric antibodies having mouse variable regions and human constant regions. Rodwell, Nature 342:99-100, 1989, discusses lower molecular weight recognition elements derived from antibody CDR information. Clackson, Br. J. Rheumatol. 3052: 36-39, 1991, discusses genetically engineered monoclonal antibodies, including Fv fragment derivatives, single chain antibodies, fusion proteins chimeric antibodies and humanized rodent antibodies. Reichman et al., Nature 332: 323-327, 1988 discloses a human antibody on which rat hypervariable regions have been grafted. Verhoeyen, et al., Science 239:1534-1536, 1988, teaches grafting of a mouse antigen binding site onto a human antibody.

(iv) Small Molecule Drugs

In some embodiments, the Isl1 modulating agent is a small molecule drug that increases the activity and/or expression of Isl1. For example, US2008/0108090 describes identification of a GSK-3β inhibitor (BIO) that could increase the expression and activity of Isl1 in cardiac progenitor cells.

In some embodiments, such small molecule drugs can be identified using the drug screening methods described herein, e.g., using Isl-TG or cells obtained therefrom.

In some embodiments, the invention contemplates a method for identifying an effective nonpeptide small-molecule inhibitor that promotes increased Isl1 activity and/or expression in an auditory hair cell or a cell with, or that is capable of differentiating into a cell with, one or more characteristics of an auditory hair cell.

Subject Selection

In some embodiments, the methods, compounds, and compositions described herein can be used for treating subjects who have, or who are at risk for developing, hearing loss, e.g., ARHL, and/or NIHL.

In some embodiments, the present invention can be used to treat hair cell loss and any disorder that arises as a consequence of hair cell loss in the ear, such as hearing impairments, deafness, and vestibular disorders, for example, by promoting differentiation (e.g., complete or partial differentiation) of one or more cells into one or more cells capable of functioning as sensory cells of the ear, e.g., hair cells.

In some embodiments, the methods include steps of selecting a subject at risk of hearing loss. Alternatively or in addition, the methods include steps of selecting a subject at risk of hair cell loss. A human subject having or at risk for developing hearing loss or hair cell loss can hear less well than the average human being, or less well than a human before experiencing the hearing loss (For example, hearing can be diminished by at least 5, 10, 30, 50% or more) or any subject that has not experienced hair cell loss or hearing loss but that will be exposed to noise (e.g., noise equal to or above a selected level or that will be exposed to loud noise for an abnormal time period).

In some embodiments, the subject can have hearing loss, which results from damage or malfunction of the sensory part (the cochlea) or the neural part (the auditory nerve) of the ear. Alternatively or in addition, the subject can have mixed hearing loss caused by a problem in both the conductive pathway (in the outer or middle ear) and in the nerve pathway (the inner ear).

In some embodiments, the subject can be deaf or have a hearing loss as a result of a traumatic event, such as a physical trauma to a structure of the ear, or a sudden loud noise, or a prolonged exposure to loud noises. For example, prolonged exposures to concert venues, airport runways, and construction areas can cause inner ear damage and subsequent hearing loss.

In some embodiments, a subject can have a hearing disorder that results from aging. Alternatively or in addition, the subject can have tinnitus (characterized by ringing in the ears).

In some embodiments, a subject suitable for treatment using the methods and compounds featured in this disclosure can include a subject having a vestibular dysfunction, including bilateral and unilateral vestibular dysfunction. Vestibular dysfunction is an inner ear dysfunction characterized by symptoms that include dizziness, imbalance, vertigo, nausea, and fuzzy vision and may be accompanied by hearing problems, fatigue and changes in cognitive functioning. Vestibular dysfunction can be the result of a genetic or congenital defect; an infection, such as a viral or bacterial infection; or an injury, such as a traumatic or nontraumatic injury. Vestibular dysfunction is most commonly tested by measuring individual symptoms of the disorder (e.g., vertigo, nausea, and fuzzy vision).

In some embodiments, the methods and Isl1 modulating compounds provided herein can be used prophylactically, such as to prevent hearing loss, deafness, or other auditory disorders associated with loss of inner ear function. For example, a composition containing one or more compounds can be administered with a second therapeutic, such as a therapeutic that may affect a hearing disorder. Such ototoxic drugs include the antibiotics neomycin, kanamycin, amikacin, viomycin, gentamycin, tobramycin, erythromycin, vancomycin, and streptomycin; chemotherapeutics such as cisplatin; nonsteroidal anti-inflammatory drugs (NSAIDs) such as choline magnesium trisalicylate, diclofenac, diflunisal, fenoprofen, flurbiprofen, ibuprofen, indomethacin, ketoprofen, meclofenamate, nabumetone, naproxen, oxaprozin, phenylbutazone, piroxicam, salsalate, sulindac, and tolmetin; diuretics; salicylates such as aspirin; and certain malaria treatments such as quinine and chloroquine. For example, a human undergoing chemotherapy can be treated using compounds and methods described herein. The chemotherapeutic agent cisplatin, for example, is known to cause hearing loss. Therefore, a composition containing one or more compounds can be administered with cisplatin therapy to prevent or lessen the severity of the cisplatin side effect. Such a composition can be administered before, after and/or simultaneously with the second therapeutic agent. The two agents can be administered by different routes of administration.

In some embodiments, the treatment of hearing loss or auditory hair cell loss includes steps whereby one or more Isl1 modulating compounds are administered to a subject. This method of treatment is referred to as direct therapy.

In some embodiments, the treatment of auditory hair cell loss includes steps whereby one or more target cells are contacted, e.g., in vitro, with an Isl1 modulating compound, and are then administered to the ear (e.g., the inner ear) of the subject. This method of therapy is referred to as cell therapy.

In some embodiments, the methods include steps whereby one or more target cells that have been contacted with one or more Isl1 modulating compounds, e.g., in vitro, are administered to the ear (e.g., inner ear) of a subject in combination with one or more Isl1 modulating compounds. This method of treatment is referred to as combination therapy.

Where appropriate, following treatment, the human can be tested for an improvement in hearing or in other symptoms related to inner ear disorders. Methods for measuring hearing are well-known and include pure tone audiometry, air conduction, and bone conduction tests. These exams measure the limits of loudness (intensity) and pitch (frequency) that a human can hear. Hearing tests in humans include behavioral observation audiometry (for infants to seven months), visual reinforcement orientation audiometry (for children 7 months to 3 years) and play audiometry for children older than 3 years. Oto-acoustic emission testing can be used to test the functioning of the cochlear hair cells, and electro-cochleography provides information about the functioning of the cochlea and the first part of the nerve pathway to the brain. In some embodiments, treatment can be continued with or without modification or can be stopped.

Routes of Administration

Direct Therapy

The route of administration will vary depending on the disease being treated. Hair cell loss and vestibular disorders can be treated using direct therapy using systemic administration and/or local administration. In some embodiments, the route of administration can be determined by a subject's health care provider or clinician, for example following an evaluation of the subject.

In some embodiments, one or more Isl1 modulating compounds can be administered to a subject, e.g., a subject identified as being in need of treatment using a systemic route of administration. Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

Alternatively or in addition, one or more Isl1 modulating compounds can be administered to a subject, e.g., a subject identified as being in need of treatment for hair cell loss, using a local route of administration. Such local routes of administration include administering one or more compounds into the ear of a subject and/or the inner ear of a subject, for example, by injection and/or using a pump.

In some embodiments, one or more Isl1 modulating compounds can be injected into the ear (e.g., auricular administration), such as into the luminae of the cochlea (e.g., the Scala media, Sc vestibulae, and Sc tympani). For example, one or more Isl1 modulating compounds can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlear capsule.

In some embodiments, the modes of administration described above may be combined in any order and can be simultaneous or interspersed.

Pharmaceutical Compositions

In some embodiments, one or more Isl1 modulating compounds can be formulated as a pharmaceutical composition. Pharmaceutical compositions containing one or more Isl1 modulating compounds can be formulated according to the intended method of administration.

One or more Isl1 modulating compounds can be formulated as pharmaceutical compositions for direct administration to a subject. Pharmaceutical compositions containing one or more compounds can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In some embodiments, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral.

A pharmaceutical composition can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, *Remington's Pharmaceutical Sciences,* 18th Ed., Gennaro, ed., Mack Publishing Co., Easton, Pa., 1990.

Alternatively or in addition, the pharmaceutical compositions can be formulated for systemic parenteral administration by injection, for example, by bolus injection or continuous infusion. Such formulations can be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

In addition to the formulations described previously, the compositions can also be formulated as a depot preparation. Such long acting formulations can be administered by implantation (e.g., subcutaneously). Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions formulated for systemic oral administration can take the form of tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

In some embodiments, the pharmaceutical compositions described herein can include one or more of the compounds formulated according to any of the methods described above, and one or more cells obtained to the methods described herein.

Cell Therapy

In some embodiments, one or more Isl1 modulating agents can be used to treat a cell in vitro (e.g., an auditory hair cell or a cell with, or that is capable of acquiring, one or more characteristics of an auditory hair cell). Such cells can then be transplanted or implanted into a subject in need of such treatment. The cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described below.

Implantation Methods

In some embodiments, cells contacted in vitro with one or more Isl1 modulating agents can be transplanted or implanted, such as in the form of a cell suspension, into the ear by injection, such as into the luminae of the cochlea. Injection can be, for example, through the round window of the ear or through the bony capsule surrounding the cochlea. The cells can be injected through the round window into the auditory nerve trunk in the internal auditory meatus or into the scala tympani.

In some embodiments, the cells described herein can be used in a cochlear implant, for example, as described in Edge et al., (U.S. Publication No. 2007/0093878).

Combination Therapies

In some embodiments, the present invention provides methods for treating a subject with one or more compounds using the direct administration and cell therapy methods described above.

US 2006/0024278 provides data suggesting that decreasing the level or activity of retinoblastoma protein in ear hair cells can regenerate inner ear hair cells, and accordingly, also provides methods for treating hearing loss in a subject by decreasing the expression or activity of retinoblastoma protein in the inner ear cells of the subject. The treatment methods described herein can be combined with the treatment methods described in US 2006/0024278 to treat hearing loss.

Effective Dose

Toxicity and therapeutic efficacy of the compounds and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any compound used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. A subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

Generally the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: *Remington's Pharmaceutical Sciences*, 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: *Goodman & Gilman's "The Pharmacological Basis of Therapeutics"*, 9th Ed., Hardman et al., eds., McGraw-Hill, New York, N.Y., 1996).

Methods of Screening

Included herein are methods for screening test compounds, e.g., polypeptides, polynucleotides, inorganic or organic large or small molecule test compounds, to identify agents that increase Isl1 expression or activity and are therefore likely to be useful in the treatment of hearing loss disorders e.g., NIHL or ARHL.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

For example, in one embodiment, a general library of small molecules is screened, e.g., using the methods described herein.

In some embodiments, a test compound is applied to a test sample, e.g., a cell or living tissue or organ, e.g., an inner ear, and one or more effects of the test compound is evaluated. In a cultured or primary cell for example, the ability of the test compound to increase Isl1 expression or activity can be evaluated.

In some embodiments, the test sample is, or is derived from (e.g., a sample taken from) an in vivo model of a disorder as described herein. For example, an animal model, e.g., a rodent such as a mouse or rat, can be used.

Methods for evaluating each of these effects are known in the art. For example, ability to modulate expression of a protein can be evaluated at the gene or protein level, e.g., using quantitative PCR or immunoassay methods. In some embodiments, high throughput methods, e.g., protein or gene chips as are known in the art (see, e.g., Ch. 12, Genomics, in Griffiths et al., Eds. *Modern genetic Analysis,* 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual,* Cold Spring Harbor Laboratory Press; 2002; Hardiman, *Microarrays Methods and Applications: Nuts & Bolts,* DNA Press, 2003), can be used to detect an effect on Isl1 expression or activity. Ability to modulate signaling via the kallikrein/kinin pathway can be evaluated, e.g., using liberation of bradykinin or other proteolytic products of kininogen (see, e.g., Campbell et al., Braz J Med Biol Res. 2000 June; 33(6):665-77), and using the measurement of cyclic guanine monophosphate (cGMP). Vascular permeability can be evaluated, e.g., as described herein.

A test compound that has been screened by a method described herein and determined to increase Isl1 expression or activity can be considered a candidate compound. A candidate compound that has been screened, e.g., in an in vivo model of a disorder, e.g., ARHL or NIHL, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that increase Isl1 expression or activity) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with hearing loss, as described herein, e.g., NIHL or ARHL. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of a disorder associated with hearing loss, as described herein. The animal can be monitored for a change in the disorder, e.g., for an improvement in a parameter of the disorder, e.g., a parameter related to clinical outcome. In some embodiments, the parameter is hearing, and an improvement would be an improvement in hearing ability (e.g., as demonstrated using an ABR or DPOAE test). In some embodiments, the subject is a human, e.g., a human with NIHL or ARHL, and the parameter is hearing ability.

In some embodiments, Isl1 modulating agents can be identified using an animal model, e.g., a wild type or transgenic mouse, e.g., an Isl1-TG mouse as described herein, or cells expressing Isl1, e.g., cells obtained (e.g., isolated and/or purified) from a wild-type mouse or from a transgenic mouse, e.g., the Isl1-TG model described herein. As described herein, the Isl1-TG animal model is a murine animal model in which Isl1 is overexpressed exclusively in auditory hair cells in the cochlear and vestibular system by way of a Pou4F3 promoter. Isl1 expression in the Isl1-TG model can be examined by way of green fluorescent protein (GFP) expression.

In some embodiments, the agents are identified using cells, e.g., cells that are from a human or mouse, e.g., hair cells differentiated in vitro from human progenitor or stem cells. For example, cells that express endogenous Isl1, or exogenous Isl1, or a reporter gene (e.g., luciferase) driven by an Isl1 promoter, can be used. The Isl1 promoter region, e.g., the region upstream of an Isl1 start codon, can be isolated, e.g., amplified from genomic DNA using appropriate primers, and cloned using methods known in the art. It has been shown that a 5 kb genomic region upstream of the Isl1 start codon contains two conserved LEF-1 sites (ACAAAGG, identical between human and mouse) that are part of the Isl1 promoter. See, e.g., Lin et al., PNAS, 104(22):9313-9318 (2007). Expression of Isl1 or the reporter gene can be assayed using methods known in the art or described herein. The screening methods can include providing such a cell, contacting the cell with a test compound, and selecting a compound if it increases Isl1 expression in the cell.

In some embodiments, candidate Isl1 modulating agents can be administered to wild type animals (e.g., locally to the ear (e.g., the inner ear) or systemically) or can be used to treat cultured cells (e.g., auditory hair cells) obtained from wild type or hearing loss animal models. Isl1 expression or hearing can then be monitored in treated animals or cells. In some embodiments, compounds that increase Isl1 activity or expression can be identified by an increase in Isl1 protein expression in auditory hair cells. In some embodiments, compounds that increase Isl1 activity or expression can be identified by detecting an increase in the expression and/or activity of a downstream target of Isl1. In some embodiments, compounds that increase Isl1 activity or expression can be identified or further evaluated by assessing the function of the compound in a wild type or Isl1-TG animal or a wild-type or Isl1-TG derived cells. For example, such function can be assessed by observing an animal's ability to hear.

Methods of Diagnosis

Included herein are methods for determining a subject's risk of developing hearing loss. The methods include obtaining a sample from a subject, and evaluating the presence and/or level of Isl1 in the sample, and comparing the presence and/or level with one or more references, e.g., a control reference that represents a normal level of Isl1, e.g., a level in a subject who has normal hearing, and/or a disease reference that represents a level of the proteins associated with high susceptibility to NIHL or severe ARHL. The presence and/or level of Isl1 can be evaluated using methods known in the art, e.g., using quantitative immunoassay methods. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of Isl1.

In some embodiments, the presence and/or level of Isl1 is comparable to the presence and/or level of the protein(s) in the disease reference, and the subject has one or more symptoms associated with ARHL or NIHL, then the subject has ARHL or NIHL. In some embodiments, the subject has no overt signs or symptoms of ARHL or NIHL, but the presence and/or level of one or more of Isl1 is comparable to the presence and/or level of Isl1 in the disease reference, then the subject has an increased risk of developing ARHL or NIHL. In some embodiments, the sample includes cells from the subject. In some embodiments, once it has been determined that a person has ARHL or NIHL or an increased risk of developing ARHL or NIHL, then a treatment, e.g., as known in the art or as described herein, can be administered.

EXAMPLES

The invention is further described in the following examples, which do not limit the scope of the invention described in the claims.

Example 1

Generation of an Isl1 Transgenic Animal Model

A transgenic mouse model in which Isl1 was overexpressed in hair cells under the control of the Pou4f3 promoter was created. Green fluorescent protein (GFP) co-expression with the Isl1 was achieved using an IRES (Internal Ribosome Entry Segment) expression cassette (Mosser et al., BioTechniques 22(1): 150-61 (1997)). The IRES is a sequence that supports translation initiation from the second cistron in a dicistronic message. Both Isl1 and the GFP were placed under the control of the Pou4f3 promoter, for hair-cell specific expression, allowing the GFP to be used as a marker for the transgene. FIG. 1 shows the construct used to create Isl1-transgenenic mice (Isl1-TG).

Genotype analysis performed using standard methods indicated the presence of the transgene (FIG. 2A). FIG. 2B shows the results of RT-PCR from utricle showed overexpression of Isl1 in Isl1-TG mice, with Myo7a as a control to normalize mRNA from hair cells. The samples are the same as in FIG. 2A.

Fluorescence microscopic detection of the GFP signal showed the expression of Isl1 transgene was hair cell specific in P3 Isl1-TG utricle and cochlea, whereas at 1 month GFP was maintained in the utricular hair cells but was strongly expressed only in the inner hair cells in the cochlea. Phalloidin staining showed normal hair bundles in 1-month-old Isl1-TG inner ear. Immunostaining with an Isl1 antibody showed overexpression of Isl1 in P2 Isl1-TG hair cells and little expression in the wild-type hair cells. Co-localization of Isl1 and GFP was seen in the utricle, illustrating that GFP signal reflects Isl1 expression Immunostaining of PCNA and GFP antibodies in P2 cochlea of Isl1-TG (TG) or control (WT) mice showed no cell proliferation in the organ of Corti.

Immunostaining showed no change of later hair cell markers prestin, Ptprq, supporting cell markers Prox1, p27, and neuronal markers acetylated tubulin, NF—H in P2 cochlea of Isl1-TG or control (WT) mice.

Thus, the expression of the Isl1 transgene was hair cell specific and persisted in adult animals. The inner ear of the transgenic mice was grossly normal without morphological abnormality. Overexpression of Isl1 did not alter expression of Lhx3 and other hair cell markers.

Isl1 hair cell specific transgenic mouse model (Isl1-TG) is immensely valuable in the studies of ARHL and NIHL. The use of this model also suggests that other models that utilize Isl1 function can be created, including an inducible Isl1 transgenic model.

Example 2

Isl1 and Age-Related Hearing Loss (ARHL)

The causes for ARHL are heterogeneous. Mutations in mitochondrial genes can give rise to ARHL, and mutations in certain genes can lead to ARHL. It is unknown, however, about the distribution of different types of ARHL and their causes. Heatshock protein has been found to be associated with a subtype of ARHL. Application of a heatshock inducer, geranylgeranylacetone, was found to attenuate ARHL to a limited degree (Mikuriya et al, Brian Res. 1212:9-17, 2008).

The effects of Isl1 expression on age-related hearing loss (ARHL) and noise-induced hearing loss (NIHL) were evaluated in the Isl1-TG transgenic mice using ABR (Acoustic Brainstem Response) and distortion product otoacoustic emissions (DPOAE). ABRs represent the summed activity of auditory neurons and thus require functional integrity of all preneural elements (including both outer and inner hair cells), as well as their afferent innervations. DPOAE arises from normal cochlear nonlinearities generated by transduction in outer hair cells and are not affected by damage to inner hair cells or cochlear neurons (see, e.g., Liberman et al., Aud Neurosci, 3:255-268 (1997)). Comparison of threshold shifts seen via the two measures thus provides important clues as to the site(s) of dysfunction.

As shown in FIGS. 3A-3D, ABR and DPOAE tests were performed at 3, 6, 8, 12 months. The ABR thresholds of Isl1-TG mice were significantly lower than control starting from 6 months across most of frequencies (3A). DPOAE threshold shift differences between Isl1-TG and control mice were also observed (3D), suggesting that the outer hair cell function may play a role in the protection effect.

Hearing tests (auditory brainstem response, or ABR) showed that during aging (from 6-month onwards), Isl1 transgenic mice have better hearing (lower ABR threshold) than wild type controls across all frequencies, whereas at young age (3-month) the ABRs for both groups were indistinguishable. Thus sustained Isl1 expression in hair cells may slow down the age-related hearing loss. It was hypothesize that sustained Isl1 expression in adult hair cells may maintain expression of some early developmental genes, which may contribute to better hearing in aged mice.

These results indicate that, overexpression of Isl1 in hair cells results in hearing preservation, and may protect against noise induced hearing loss.

Figures 4A, 4B, 4C, 4D, 4E, 4F:
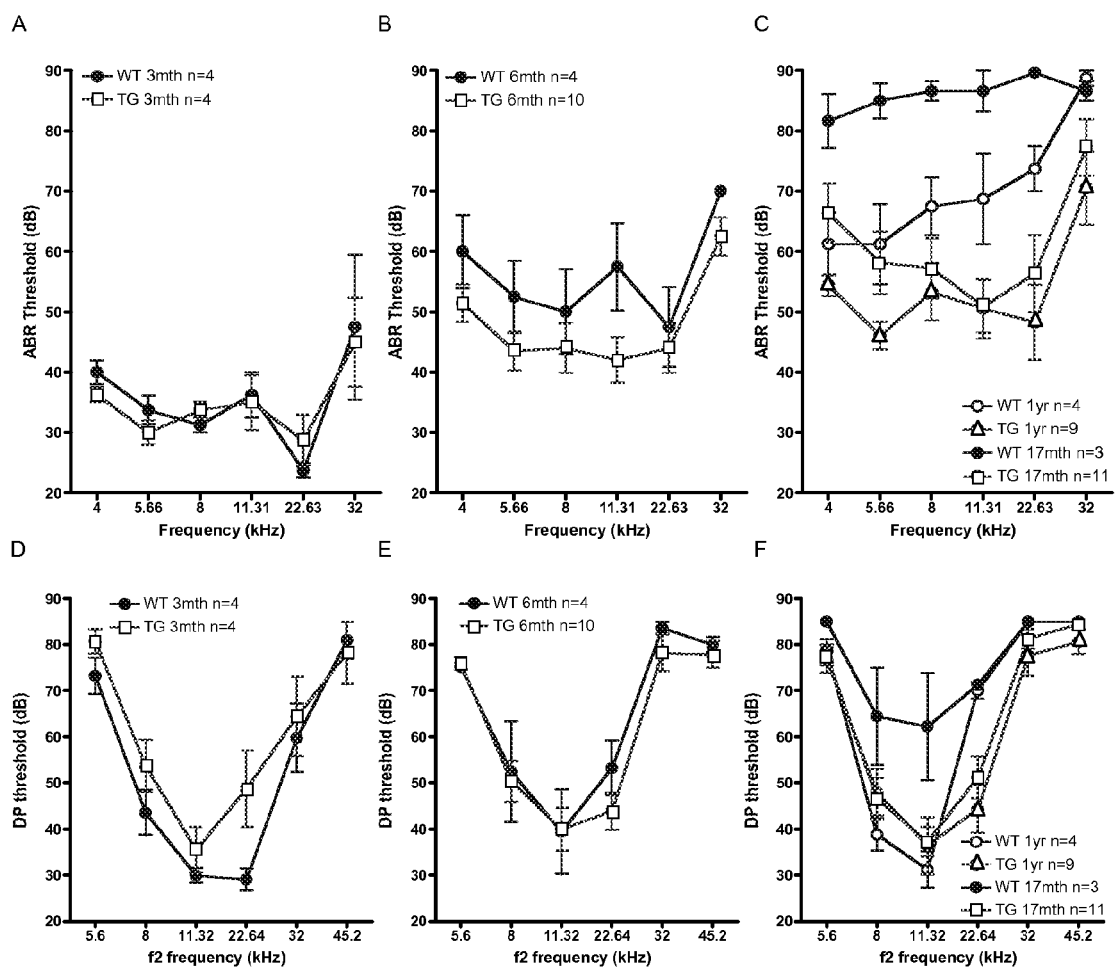
FIGS. 4A-F are line graphs showing the results of ABR and DPOAE tests performed at 3, 6, 12 and 17 months. (4A) ABR at 3 months; (4B) ABR at 6 month; (4C) ABR at 12 and 17 months; (4D) DPOAE at 3 months; (4E) DPOAE at 6 months; (4F) DPOAE at 12 and 17 months.
Figure 5A:
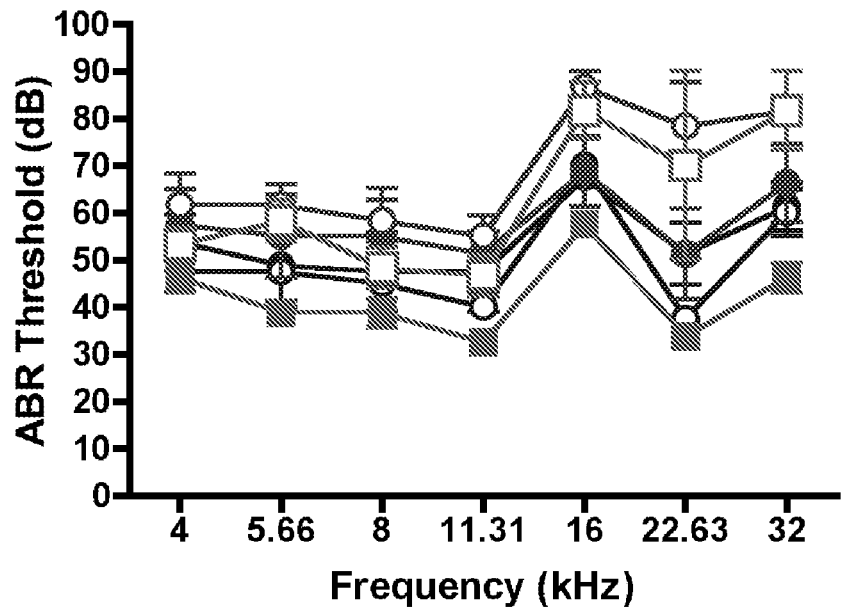
FIGS. 5A-D are line graphs showing the results of ABR (5A) and DPOAE (5B) tests performed before and after 8-week-old Isl1-TG and control littermates were exposed to noise (8-16 kHz octave-band, 100 dB SPL, 2 hours). The thresholds of ABR and DPOAE were recorded 1 week pre- and 1 and 2 weeks post-exposure. In contrast to control mice with permanent shifts of both ABR (5C) after noise exposure, Isl1-TG mice did not exhibit little ABR threshold change, indicating strong protection against noise-induced hearing loss. In contrast to control mice with DPOAE shift after noise exposure, DPOAE shifted to the opposition direction indicating better outer hair cell function (5D).
Figure 5B:
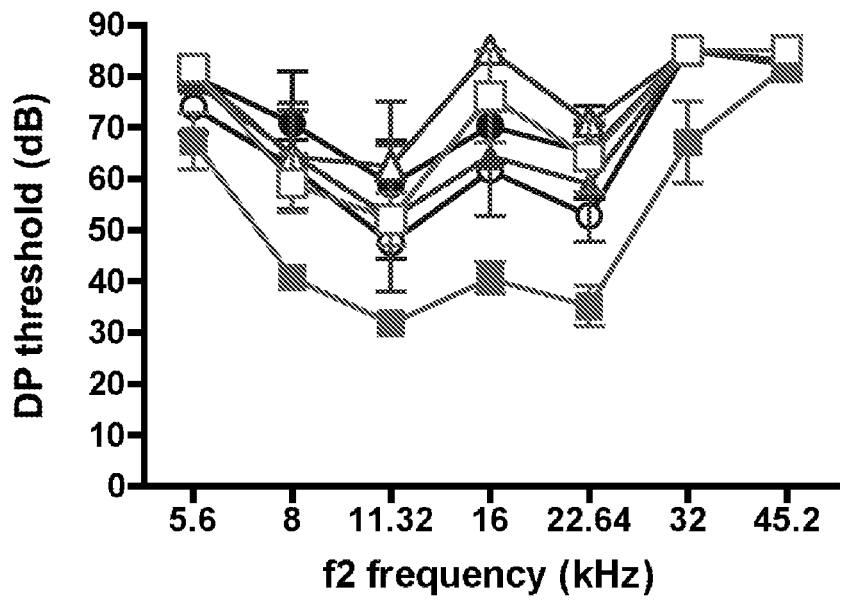
Figure 5C:
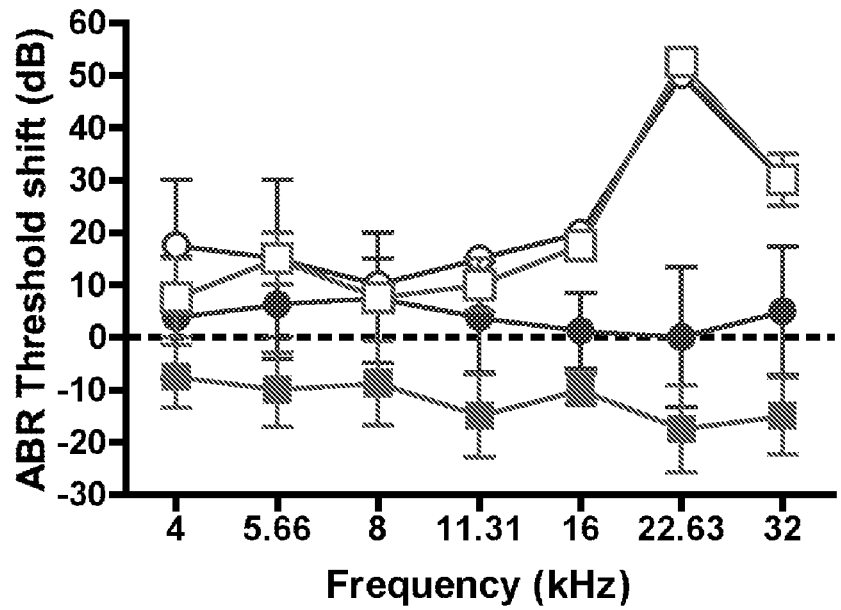
Figure 5D:
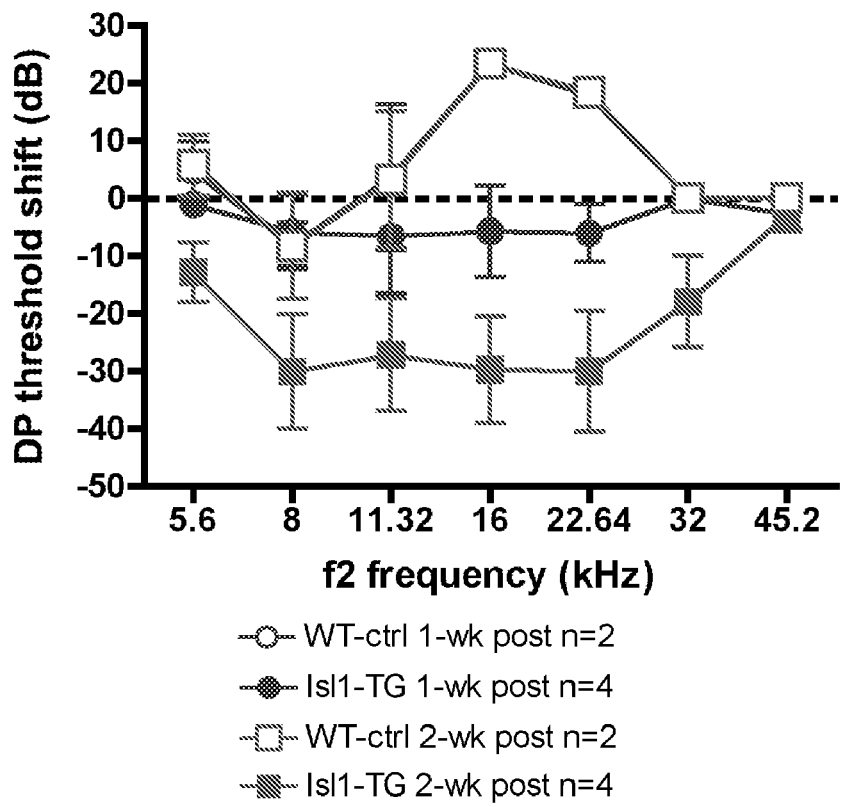

Further, ABRs and DPOAEs were recorded on the same litter of mice at 3, 6, 8, 12, 17 months. The littermates were used to minimize the hearing test bias due to background variation. At 3 months of age, the ABRs in both Isl1-TG mice and their control littermates were indistinguishable (FIG. 4A). By 6 months of age, significant ABR threshold shift of over 20 dB was observed in control across all frequencies, whereas an average of 10 dB threshold shift was observed in Isl1-TG mice (FIG. 4B). ARHL progressed steadily at 12 and 17 months of age in control mice, with an average of threshold shift of 30 dB and 50 dB, comparing to 3 months of age (FIG. 4C). Strikingly in the Isl1-TG mice, the threshold shift was relatively unchanged between 6 and 12 months, and only slightly elevated at 17 months at lower frequencies (FIG. 4C). ARHL was significantly attenuated in the Isl1-TG mice from 6 months onwards, with the most dramatic effects at 17 months of age.

To understand the potential source of ARHL, the DPOAE was performed with the same group of mice. DPOAE thresholds in Isl1-TG mice were initially slightly higher than controls at 3 months (FIG. 4D) but became indistinguishable from control at 6 or 12 months (FIG. 4E,F). At 17 months, DPOAE threshold shifted significantly in control but remained stable in Isl1-TG mice (FIG. 4F), suggesting that outer hair cell dysfunction may partially contribute to severe ARHL at later stages in control mice and Isl1 may protect outer hair cells from such dysfunction.

These results suggest that Isl1 plays a significant role in attenuating ARHL related to neuronal defect, as overexpression of Isl1 has a protective role in significantly reducing the progression of ARHL.

Example 3

Isl1 and Noise-Induced Hearing Loss (NIHL)

The hearing of Isl1-TG and control mice exposed to noise was evaluated for NIHL. Multiple mechanisms have been identified for NIHL. They include hair cell death, reactive oxygen species (ROS) formation, decreased blood flow in the cochlea, elevated glucocorticoid plasma concentration, glutamate excitotoxicity, calpain and calcineurin-mediated cell death, caspase-dependent cell death, mitochondria-mediated cell death, and activation of JNK pathway (Le Prell et al, Hear Res., 226:22-43, 2007). Various strategies have been developed to reduce the effects of the mechanisms in order to offer protection from NIHL (see, e.g., Le Prell et al, supra).

Hearing of 7-week-old mice was tested using ABD and DPOAE before they were exposed to loud noise for an extended period of time (2 hours). Subsequently ABR and DP were performed one and two weeks after, to measure permanent threshold shift.

The results are shown in FIGS. 5A-D. In control mice, significant hearing loss (permanent threshold shift) was recorded at both time points (5C-D). In contrast, in the Isl1-TG mice, little ABR shift was detected one week after noise exposure. Furthermore, ABR (5A) performed at two weeks showed even better hearing than before noise exposure. Dramatic DPOAE threshold shift (5D) was observed in control mice subjected to noise damage, but no such change was observed in Isl1-TG under the same condition.

These results indicate that Isl1 plays an essential role in protecting hearing loss caused by cochlear epithelial cell defects due to loud noise. Combined, these results demonstrate that Isl1 expression in hair cells protects the inner ear from NIHL.

It is surprising that the function of Isl1 in hair cells could have such profound effects in protection of ARHL and NIHL, likely through distinct mechanisms with the targets in cochlear epithelial cells and neurons, respectively. The protection against NIHL seems to be very robust. The fact that Isl1 overexpression can protect both ARHL and NIHL indicates that either a similar mechanism is involved in two types of hearing loss, or the function of Isl1 involves multiple mechanisms.

These data suggest that activation of Isl1 function in mammalian hair cells has dual roles in slowing the progression of ARHL and protection of hearing from NIHL. This is a clear advantage as previously no method has been reported to protect inner ear from both ARHL and NIHL. Furthermore, the protection of NIHL by Isl1 is drastic. These results also indicate that additional inducible Isl1 mouse models could be produced, so that short- and long-term activation of Isl1 can be evaluated during different stages of ARHL and NIHL, to precisely determine the role of Isl1 in protection of hearing from aging and noise damage. Small molecules, miRNA or other reagents with similar effect as Isl1 could be used as drugs to achieve similar effects as Isl1-TG in hearing protection against ARHL and NIHL. Further both the genes that control Isl1 expression and downstream Isl1 target genes can be manipulated similarly to achieve protection against ARHL and NIHL.

These results also suggest that Isl1 can be used as a therapeutic target to treat or prevent both ARHL and NIHL.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying a candidate compound for promoting auditory hair cell viability, the method comprising:
   i) providing a differentiated auditory hair cell;
   ii) contacting the differentiated auditory hair cell with a test compound;
   iii) detecting the expression of Islet 1 (Isl1) in the differentiated auditory hair cell;
   iv) selecting a test compound that increases the expression or the activity of Isl1 in the differentiated auditory hair cell as compared to the expression or the activity of Isl1 in the absence of the test compound; and
   v) testing the selected test compound that increases the expression or the activity of Isl1 from step iv) for its ability to promote viability of differentiated auditory hair cells.

2. A method for identifying a candidate compound for promoting auditory hair cell viability, the method comprising:
   i) providing a differentiated auditory hair cell that expresses a reporter gene under the control of an Isl1 promoter;
   ii) contacting the differentiated auditory hair cell with a test compound;
   iii) detecting the expression of the reporter gene in the differentiated auditory hair cell;
   iv) selecting a test compound that increases the expression of the reporter gene in the differentiated auditory hair cell as compared to the expression level of the reporter gene in the absence of the test compound; and v) testing the selected test compound that increases the expression of the reporter gene from step iv) for its ability to promote viability of differentiated auditory hair cells.

3. The method of claim 1, further comprising:

administering the selected test compound that increases the expression or the activity of Isl1 from step iv) to a test animal;

detecting the expression of Isl1 in auditory hair cells of the test animal; and selecting a test compound that increases the expression Isl1 in the auditory hair cell of the test animal as compared to the expression of Isl1 in the absence of the test compound as a candidate compound for promoting auditory hair cell viability.

4. The method of claim 2, further comprising:

selecting a test compound that increases the expression of the reporter gene in the hair cell;

administering the selected test compound that increases the expression of the reporter gene from step iv) to a test animal;

detecting the expression of Isl1 in auditory hair cells of the test animal; and selecting a test compound that increases the expression of Isl1 in the auditory hair cell of the test animal as compared to the expression of Isl1 in the absence of the test compound as a candidate compound for promoting auditory hair cell viability.

5. The method of claim 1, wherein the differentiated auditory hair cell is a cultured hair cell.

6. The method of claim 1, wherein the differentiated auditory hair cell is from an Isl-1 transgenic animal.

7. The method of claim 1, wherein the differentiated auditory hair cell is a human cell.

8. The method of claim 1, wherein the differentiated auditory hair cell is from a wild-type or transgenic mouse.

9. The method of claim 1, wherein the differentiated auditory hair cell is differentiated in vitro from human progenitor or stem cells.

10. The method of claim 2, wherein the differentiated auditory hair cell is a cultured hair cell.

11. The method of claim 2, wherein the differentiated auditory hair cell is from an Isl-1 transgenic animal.

12. The method of claim 2, wherein the differentiated auditory hair cell is a human cell.

13. The method of claim 2, wherein the differentiated auditory hair cell is from a wild-type or transgenic mouse.

14. The method of claim 2, wherein the differentiated auditory hair cell is differentiated in vitro from human progenitor or stem cells.

15. The method of claim 3, wherein the test animal is a wild type or transgenic mouse.

16. The method of claim 15, wherein the transgenic mouse is an Isl-1 transgenic mouse.

17. The method of claim 4, wherein the test animal is a wild type or transgenic mouse.

18. The method of claim 17, wherein the transgenic mouse is an Isl-1 transgenic mouse.

19. The method of claim 1, further comprising testing the selected compound that increases the expression or activity of Isl1 from step iv) for its therapeutic efficacy for treating age-related or noise-induced hearing loss.

20. The method of claim 2, further testing the selected compound that increases the expression or activity of the reporter gene from step iv) for its therapeutic efficacy for treating age-related or noise-induced hearing loss.

21. The method of claim 3, further comprising testing the selected compound that increases the expression of Isl1 in the auditory hair cell of the test animal for its therapeutic efficacy for treating age-related or noise-induced hearing loss.

22. The method of claim 4, further comprising testing the selected compound that increases the expression of Isl1 in the auditory hair cell of the test animal for its therapeutic efficacy for treating age-related or noise-induced hearing loss.

* * * * *